United States Patent [19]

Igoe

[11] Patent Number: 4,755,181
[45] Date of Patent: Jul. 5, 1988

[54] ANTI-SUTURE LOOPING DEVICE FOR PROSTHETIC HEART VALVES

[75] Inventor: Timothy M. Igoe, Lakewood, Colo.

[73] Assignee: Matrix Medica, Inc., Wheat Ridge, Colo.

[21] Appl. No.: 105,898

[22] Filed: Oct. 8, 1987

[51] Int. Cl.⁴ ............................................. A61F 2/24
[52] U.S. Cl. ................................... 623/2; 128/303 R
[58] Field of Search ............ 623/2; 128/303 R, 334 R

[56] References Cited

U.S. PATENT DOCUMENTS

| | | | |
|---|---|---|---|
| 4,585,453 | 4/1986 | Martin | 128/303 R |
| 4,683,883 | 8/1987 | Martin | 623/2 |
| 4,702,250 | 10/1987 | Ouil | 128/303 R |

FOREIGN PATENT DOCUMENTS 2169386  7/1986  United Kingdom ................. 623/2

Primary Examiner—Richard J. Apley
Assistant Examiner—James Prizant
Attorney, Agent, or Firm—Dressler, Goldsmith, Shore, Sutker & Milnamow, Ltd.

[57] ABSTRACT

An anti-suture looping device for prosthetic polycuspid heart valves is provided. The device comprises a frame or body portion that is attached to the heart valve assembly and a vaned insert portion that can project beyond the cusps of the heart valve. The insert portion can slide within the body portion between a retracted position where the vanes do not project beyond the free ends of the cusps of the valve and a forward position where the vanes pass between the cusps of the valve, extend beyond, and protect the cusps from interference or damage by any suture loops that may catch on the cusps when the heart valve assembly is secured into place.

13 Claims, 2 Drawing Sheets

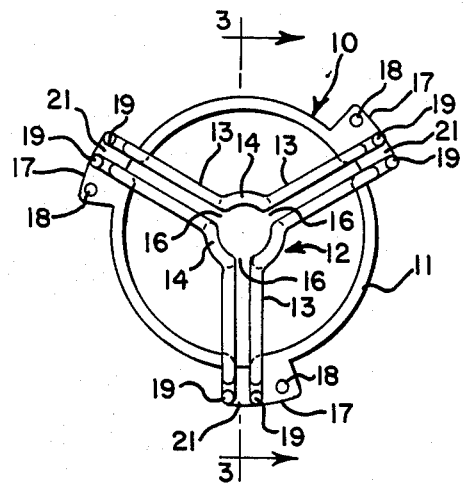
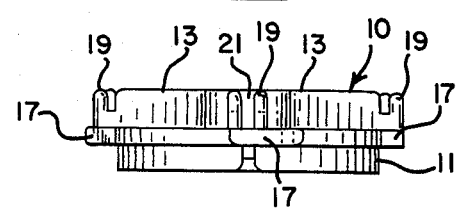
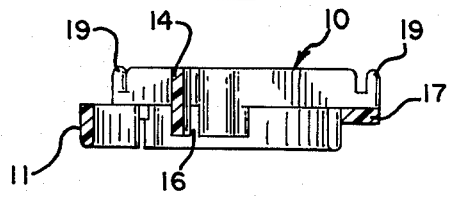
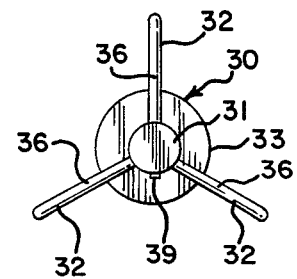
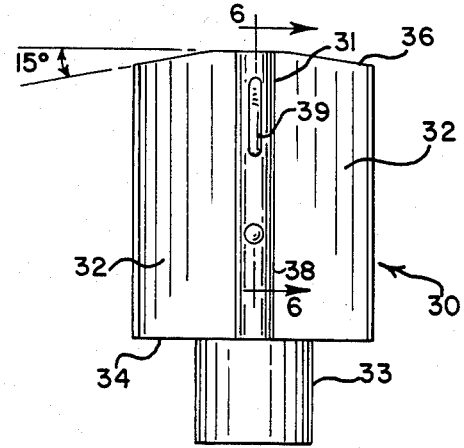
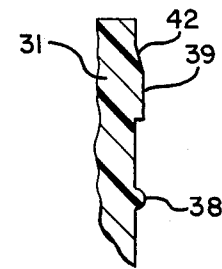

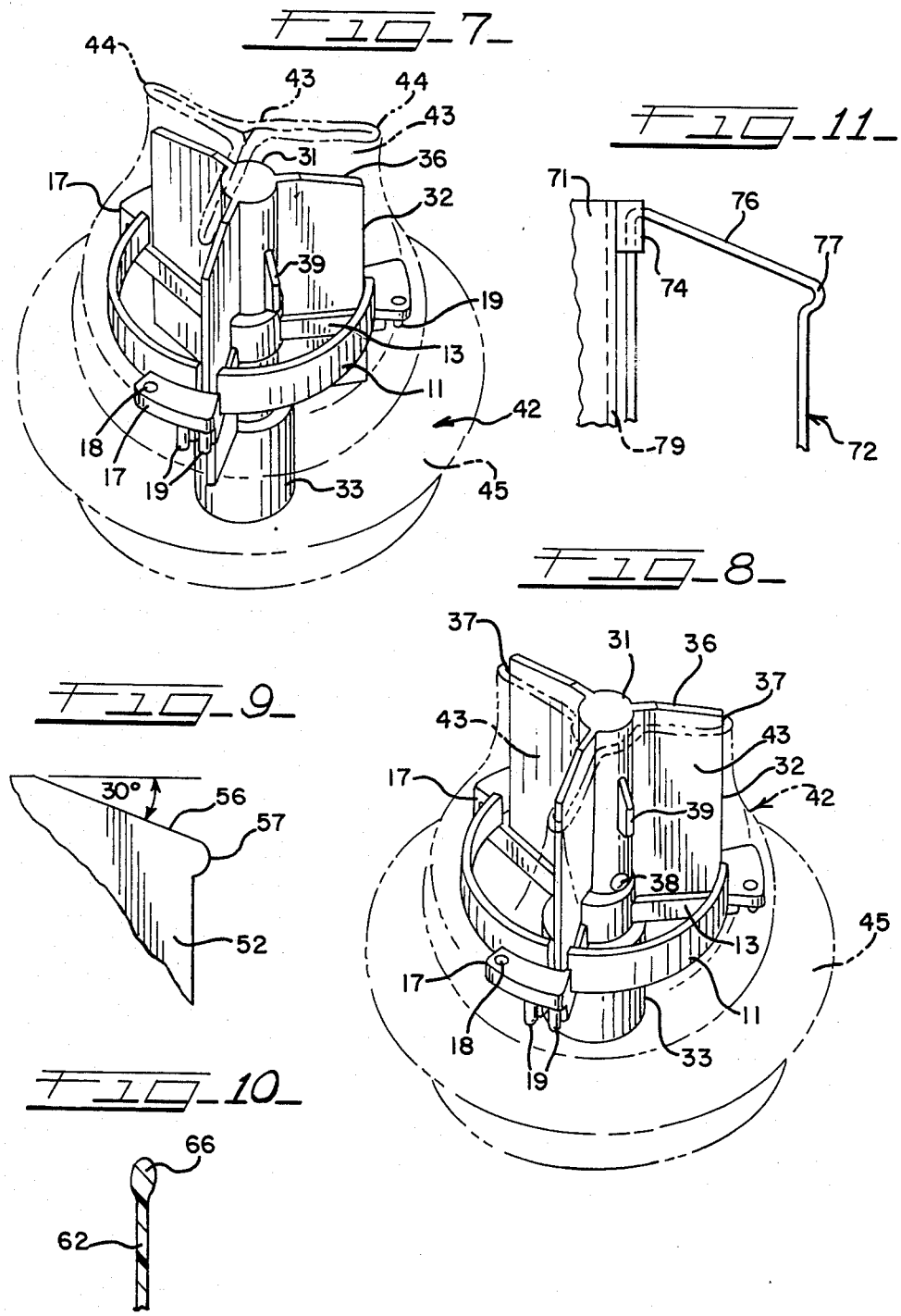

ANTI-SUTURE LOOPING DEVICE FOR PROSTHETIC HEART VALVES

BACKGROUND OF THE INVENTION

1. Field of the Invention

This invention relates to a device for protecting the cusps of prosthetic heart valves from interference by suture looping during the implantation or attachment of the valve to the heart tissue of the patient.

2. Description of the Prior Art

Heart valve prostheses are of two general types, mechanical valve protheses and natural tissue prostheses. Natural tissue prostheses are generally considered to be preferable with respect to similarity to natural flow characteristics, minimal thrombogenicity and low incidence of catastrophic in vivo dysfunction.

Pericardial tissue valves and heart valves taken from pigs, suitably processed, are used for implantation in human patients as prosthetic heart valves. These heart valves have plural cusps which are normally in contact with each other at the free ends of the cusps to maintain the valve in normally closed position. However, the cusps are flexible and are forced apart from each other at their free ends, temporarily, by blood pressure engendered by each heartbeat. Illustrative of such prosthetic heart valves are those shown in U.S. Pat. No. 4,477,930 to Totten, et al Natural tissue heart valves usually have a cloth or fabric covered framework, known as a stent, which incorporates a suture ring at its base so as to facilitate its implantation into the annulus or wall of the heart, using conventional surgical procedures.

When the heart valve is positioned in the mitral valve annulus for surgical implantation by suturing its suture ring to the annulus, the valve cusps face away from the surgeon, and the space beyond the valve cusps (within the heart cavity) is hidden from the view of the surgeon. It is therefore possible that a suture loop formed during the suturing procedure may extend beyond the free ends of the cusps and may become entangled in one or more of the cusps when the loop is reduced in size as the suture needle is pulled to tighten the stitch. Such entanglement interferes with the intended operation of the valve and may result in damage to the valve cusps, thereby making the valve unsuitable for its purpose.

This invention provides a device for the protection of a natural tissue heart valve, synthetic leaflet heart valves, or the like, from interference or damage by suture looping.

SUMMARY OF THE INVENTION

The present invention contemplates a device that can be inserted into a polycuspid prosthetic heart valve assembly to protect the valve cusps from suture looping interference while the valve assembly is secured into place.

The protective device comprises a frame portion and a vaned insert element slidably received within the frame portion. The vaned insert element is positionable in an extended position and a retracted position relative to the frame portion. The vaned insert element is in its extended position while the valve assembly is implanted into a patient.

The frame portion includes an annular positioning element that is sized for placement within a stitchable periphery of the prosthetic valve assembly, and a hollow hub for the positioning element. The hollow hub is connected to the positioning element with plural spokes that extend radially from the hub to the annular positioning element.

The vaned insert element includes a central post that is slidably received within the hollow hub and plural vanes that are peripherally spaced about the central post. The number of vanes in each instance is determined by the number of valve cusps present. The vanes extend radially outwardly from the central post and are dimensioned so that a portion of each vane projects beyond one of the valve cusps when the vaned insert element is in the extended position. The projecting vane portion serves as a camming means for guiding a suture loop away from the corresponding valve cusp. The central post at its base terminates in a collar. The central post can be threaded to accept a holding tool.

During storage, the vaned insert portion of the device is in its retracted position. It does not extend beyond the free ends of the valve cusps because having the vanes extending past the free ends of the cusps throughout the storage period separates the cusps from contact with each other and is likely to produce an undesirable set in the valve cusps beyond the ability of their natural resiliency to overcome. Also, storage of the assembly with the anti-suture looping device in its retracted position minimizes the likelihood of tissue abrasion, particulate contamination and the like.

To provide assurance that the device remains in its retracted position during storage, a detent means is provided in the form of a raised portion or protuberance on the central post. The protuberence is high enough to prevent movement of the insert portion toward its extended or forward position by gravity alone, but low enough so that the surgeon can push the insert portion to its extended position by only slight positive pressure. This detent means also serves to maintain the device in its extended position. To prevent the insert element or portion and the frame or body portion from separating from each other, this detent coacts with an abutment on the post spaced from the detent means in a direction toward the distal end of the post.

When the device of the invention is attached to the prosthetic heart valve assembly and throughout the storage period prior to installation of the valve, the device is in its retracted position. The vanes do not extend beyond the free ends of the valve cusps.

BRIEF DESCRIPTION OF THE DRAWINGS

In the drawings,

FIG. 1 is a plan view of the frame or body portion of the device of this invention;

FIG. 2 is a front elevation of the frame or body portion of the device of this invention;

FIG. 3 is a cross-sectional view taken at plane 3—3 of FIG. 1;

FIG. 4 is a plan view of the vaned insert element of the device of this invention;

FIG. 5 is a front elevation of the vaned insert element of the device of this invention;

FIG. 6 is an enlarged fragmentary cross-sectional view taken at plane 6—6 of FIG. 5;

FIG. 7 is a perspective view of the assembled device in its retracted position with a tricuspid prosthetic heart valve assembly shown in phantom;

FIG. 8 is a perspective view of the assembled device in its extended position with the heart valve assembly shown in phantom;

FIG. 9 is a fragmentary elevational view of one of the vanes, showing another embodiment of the device of the invention;

FIG. 10 is a fragmentary cross-section of one of the vanes showing yet another embodiment of the invention; and FIG. 11 is a fragmentary elevational view of yet another vane configuration in the form of a wire frame.

DETAILED DESCRIPTION OF PREFERRED EMBODIMENTS

The overall configuration of the assembled protective device embodying the present invention is illustrated in FIGS. 7 and 8 and is constituted by the structural elements illustrated in FIGS. 1 through 6.

Referring first to FIGS. 1 to 3, the frame or body portion 10 of the device of this invention for a tricuspid valve comprises an annular positioning element or body portion, such as ring 11 and hollow hub 12 connected thereto by three slotted radial arms or spokes 13, evenly spaced from each other at about 120-degree intervals. The hollow hub is defined by three arcuate portions 14 separated by spaces 16.

Each of the radial arms extends beyond ring 11 forming extension tab 17 that serves to provide securement means for the device to a stitchable periphery of the prosthetic valve assembly. Each extension 17 is provided with suture hole 18 and upstanding projections 19 to provide a channel for temporary suture securement to the valve assembly.

Slots 21 within each of radial arms 13 are aligned with hub spaces 16 so that hub 12, together with arms 13, defines a star-shaped aperture through which the vanes of insert portion 30 may pass as hereinafter described.

As shown in FIGS. 4 to 6, insert portion 30 comprises central post 31 and radial fins or vanes 32. Collar 33 of greater transverse dimension than the central post 31 defines a retaining rim and is provided at the proximal end or base of the central post. The configuration and diameter of collar 33 can vary and are selected as dictated primarily by packaging considerations. Central post 31 may include a threaded aperture therein for receiving a holding tool, e.g., handle of a valve sizing device. The central post 31 may also be provided with external threads for the same purpose, if desired.

Radial vanes 32 abut collar 33 at bottom edge 34 of each vane at the portion of the vane which is proximal to central post 31. The distal edge 36 of each vane, or the leading edge of the vane with respect to its motion as described with respect to FIGS. 7 and 8, is tapered in that it extends farther forward at a location nearer to central post 31 than at a location farther away from the central post. The degree of taper can vary; preferably the taper is at an angle of about 15 degrees from a plane normal to the longitudinal axis of central post 31 as shown in FIG. 5. In the alternate embodiment shown in FIG. 9, the taper angle is about 30 degrees. The taper preferably begins at about one-third of the distance radially outwardly from the center of the central post 31.

The insert portion 30 and the body portion 10 are assembled to form the device of this invention as shown in FIGS. 7 and 8. The leading edges of the vanes are passed through the slots of the radial arms and the central post is passed through the hollow hub of the body portion. The insert portion is then moved axially through the vane slots and the hub until a detent (to be described below) is reached at about the midpoint of the central post. This is the retracted position of the device. The device is shipped in association with its valve assembly in this position, stored and maintained. The device is changed to its extended position prior to the implantation of the valve assembly into the heart of the patient.

As may be seen in FIG. 7, the leading edges of vanes 32 do not project beyond the free ends of the valve cusps 43 when the device is in its retracted position; the cusps 43 are therefore permitted to maintain their normal closed position during the storage period.

In FIG. 8 the leading edges of vanes 32 extend beyond the free ends of the cusps 43 when the device is in its extended position and ready for attachment. The transverse dimension of the vanes is adjacent to the transverse dimension of the cusp ends. Thus, if any suture loops are formed beyond the cusps of the valve during the suturing of the valve assembly into place, these loops, as they are contracted by pulling and tightening the suture, will first contact the leading edge of a vane. Additional tightening of the suture and contraction of the suture loop will cause the suture to slide along the tapered leading edge of the vane until the suture passes the shoulder of the vane. Contraction of the suture loop is then continued beyond the transverse edge of the adjacent cusp of the valve. In the embodiment illustrated in FIG. 8 the transverse edges of the vanes are close to, but do not extend beyond, the transverse edges of the valve cusps so that small notches 37 exist just below the shoulder of each vane. As a practical matter, however, these notches are too shallow to snag a suture loop. An alternate vane profile shown in FIG. 9 eliminates any slight possibility of snagging a suture loop within the shallow notches by providing a lateral extension 57 that is described in greater detail hereinbelow.

As best seen in FIGS. 5 and 6, central post 31 is provided with protuberance 38, located just below the location of hub 12 when in the retracted position, and ridge 39, located just above the location of hub 12 in the same retracted position. Ridge 39 is tapered at slope 42 toward the end of central post 31 which is farthest from collar 33.

In the fabrication of the device, separate body and insert portions 10 and 30, are each molded from a plastic material of suitable strength, such as the thermoplastic acetal resin, commercially available under the trademark DELRIN from E. I. duPont de Nemours & Co.

The device of this invention is assembled by positioning the insert portion into the body portion with central post 31 within hollow hub 12 and with each vane 36 received within a slot 21. The two portions are then pushed toward each other so that the interior of hub 12 slides over slope 42 and ramp or ridge 39 until the hub passes ramp or ridge 39 and is located between it and protuberance 38. At this position, the hub is retained in position by protuberance 38 and the end portion of ridge 39 which serves as an abutment means. This is the retracted position for storage illustrated in FIG. 7.

FIGS. 7 and 8 show a prosthetic heart valve assembly 42 in phantom and having positioned therewithin the valve cusps protecting device of the present invention. Valve assembly 42 is provided with a stitchable peripheral suturing member such as sewing ring 45, or the like. However, a stitchable periphery can also be provided by means of pre-drilled holes in the stent.

The cusp protecting device of the present invention is positioned within the heart valve assembly 42 so that sewing ring 45 surrounds the frame portion 11 and contacts tabs 17 that are unitary therewith. Tabs 17 are provided with through apertures 18 and upstanding paired projections 19 spaced from radially extending arms or spokes 13. Frame portion 11 of the present anti-suture looping device is temporarily secured to sewing ring 45 by sutures (not shown) that pass through apertures 18 and around projections 19. After the valve assembly has been secured in place, the sutures are severed and removed, and the anti-suture looping device is lifted out from the valve assembly.

Cusps 43 of the valve are joined to each other at junctures 44. Vanes 32 are transversely dimensioned to come close to cusp junctures such as 44 and to pass therethrough when vaned insert portion 10 is pushed into the extended position as shown in FIG. 8. Vanes 32 are also dimensioned to pass through the openings between cusps 43 when the vaned insert portion is in its extended position.

FIG. 9 shows an alternative vane profile in which leading edge 56 of vane 52 extends laterally at its shoulder portion by projection 57. In this manner leading edge 56 terminates beyond the normal position of the valve cusp juncture and requires a temporary stretching of juncture as the insert portion is pushed to its forward position. It also requires a temporary stretching of the cusp juncture when the insert portion is retracted to its original position before the device is removed from the heart. The stretching in both cases is gentle, however, because the insert portion of the device is moved slowly both in pushing it to the forward position and in pulling it back to the retracted position.

When the device of FIG. 9 is in its extended position, it provides protection to the cusps of the heart valve in the same manner as the device of FIGS. 1-8, but notches between the vanes and the cusps are avoided. It thereby eliminates even the slight possibility that a suture loop may snag in one of such notches.

FIG. 10 shows leading or forward portion of an alternate vane configuration in cross section to illustrate another embodiment of the invention. The leading edge 66 of vane 62 is bulbous and rounded. Such edge configuration provides rounded edges for the vanes and further facilitates passage of the vanes through the valve cusps when the vanes are moved forward through the cusp openings and also when they are thereafter retracted.

Yet another vane configuration is illustrated in FIG. 11. Vane 72 is an open wire frame, made from, e.g., a stainless steel wire loop, that defines leading edge 76 and a knob-like projection 77. The wire frame defining vane 72 is preferably flexible or hinged for movement in the plane of the vane so that knob-like projection 77 can be depressed or shifted radially inwardly as the device is extracted following implantaton of the heart valve. Central post 71 is provided with slotted protuberance 74 within which vane 72 can be received. Also, both solid and open wire frame-type vanes can be hingedly mounted to the central post and can be partially received into appropriate longitudinal slots, such as slot 79, defined by the central post 71, during extraction.

It is to be understood that the foregoing description is intended as a description of preferred embodiments only and that various modifications may be made without departing from the spirit and scope of the present invention as defined by the appended claims.

I claim:
1. A device for protecting from interference by suture looping the cusps of a polycuspid prosthetic heart valve assembly having a stitchable periphery, which device comprises
   a frame portion; and
   a vaned insert element slidably received within said frame portion and positionable in an extended position and a retracted position relative to the frame portion:
   said frame portion comprising an annular positioning element sized for placement within said stitchable periphery, a hollow hub for said positioning element and connected thereto with plural spokes that extend radially from the hub to the positioning element; and
   said vaned insert element comprising a central post slidably received within said hollow hub and having plural vanes peripherally spaced about said post and extending radially outwardly therefrom; said vanes being dimensioned so that a portion of each vane projects beyond one of said cusps when said vaned insert element is in the extended position.

2. The device of claim 1, wherein said spokes are slotted and together with said hollow hub define a through passageway for receiving the vaned insert element therewithin.

3. The device of claim 1, wherein said central post is provided with a detent means to axial translation of said insert portion within said hub, said detent means maintaining said valved insert element in desired position.

4. The device of claim 3, wherein said central post also defines an abutment means along its length toward the distal end thereof, and at a location spaced from said detent means; said abutment means coacting with said detent means to maintain said vaned insert element in the retracted position.

5. The device of claim 3, wherein said detent means is a protuberance on the central post.

6. The device of claim 4, wherein a second abutment means is provided at the proximal end of the central post and coacts with said detent means to maintain said vaned insert element in the extended position.

7. The device of claim 1, wherein the leading edge of each of said vanes extends laterally beyond the transverse dimensions defined by the free ends of the cusps of said valve.

8. The device of claim 1, wherein said vanes are webs of substantially uniform thickness and are unitary with the central post.

9. The device of claim 1 wherein said vanes are wire frames.

10. The device of claim 1, wherein the vanes are provided with a bulbous leading edge.

11. A prosthetic heart valve kit which comprises
   a polycuspid prosthetic heart valve assembly having a stitchable periphery and defining a central passageway occluded by plural cusps; and
   an anti-suture looping device situated within said passageway and removably secured to the stitchable periphery;
   said anti-suture looping device comprising a substantially annular body portion provided with a hollow hub joined to the body portion by spaced, slotted radial arms, said slotted radial arms together with said hollow hub defining a substantially star-shaped through aperture in the body portion; and a vaned insert portion slidably mounted within said star-shaped through aperture and being positionable in a retracted position and an extended position, the vanes of said insert portion being sized to project through the cusps when the insert portion is in the extended position.

12. The prosthetic heart valve kit in accordance with claim 11, wherein the annular body portion of said anti-suture looping device is provided with plural suture securement means spaced about the periphery thereof.

13. The prosthetic heart valve kit in accordance with claim 12, wherein the plural suture securement means are evenly spaced from one another.

* * * * *